(12) United States Patent
Erikson et al.

(10) Patent No.: US 7,220,541 B2
(45) Date of Patent: *May 22, 2007

(54) HOMOGENEOUS ASSAY OF BIOPOLYMER BINDING BY MEANS OF MULTIPLE MEASUREMENTS UNDER VARIED CONDITIONS

(75) Inventors: Glen H. Erikson, Providenciales (TC); Jasmine I. Daksis, Ontario (CA); Pierre Picard, Ontario (CA)

(73) Assignee: Ingeneus, Inc., Belize (BZ)

(*) Notice: Subject to any disclaimer, the term of this patent is extended or adjusted under 35 U.S.C. 154(b) by 243 days.

This patent is subject to a terminal disclaimer.

(21) Appl. No.: 09/911,047

(22) Filed: Jul. 23, 2001

(65) Prior Publication Data

US 2002/0137056 A1  Sep. 26, 2002

Related U.S. Application Data

(63) Continuation-in-part of application No. 09/490,273, filed on Jan. 24, 2000, now Pat. No. 6,265,170.

(51) Int. Cl.
  *C12Q 1/68* (2006.01)
  *C07H 21/04* (2006.01)
  *C12P 19/34* (2006.01)
  *B32B 5/02* (2006.01)

(52) U.S. Cl. ............... 435/6; 435/283.1; 536/23.1; 536/24.32; 536/25.32; 422/82.05

(58) Field of Classification Search ............... 435/6, 435/91.1, 91.2, 7.1, 174, 283.1, 288.7; 536/24.3, 536/24.31, 23.1; 935/6; 436/518; 422/68.1, 422/82.01, 82.05

See application file for complete search history.

(56) References Cited

U.S. PATENT DOCUMENTS

| | | | |
|---|---|---|---|
| 4,220,450 A | 9/1980 | Maggio | |
| 4,876,187 A | 10/1989 | Duck et al. | |
| 4,963,477 A | 10/1990 | Tchen | |
| 5,011,769 A | 4/1991 | Duck et al. | |
| 5,332,659 A | 7/1994 | Kidwell | |
| 5,403,711 A | 4/1995 | Walder et al. | |
| 5,538,848 A | 7/1996 | Livak et al. | |
| 5,539,082 A | 7/1996 | Nielsen et al. | |
| 5,558,998 A | 9/1996 | Hammond et al. | |
| 5,660,988 A | 8/1997 | Duck et al. | |
| 5,705,346 A | 1/1998 | Okamoto et al. | |
| 5,707,801 A | 1/1998 | Bresser et al. | |
| 5,731,146 A | 3/1998 | Duck et al. | |
| 5,770,369 A * | 6/1998 | Meade et al. ............... 435/6 | |
| 5,783,063 A | 7/1998 | Clarkson et al. | |
| 5,800,984 A | 9/1998 | Vary | |
| 5,800,992 A | 9/1998 | Fodor et al. | |
| 5,814,447 A | 9/1998 | Ishiguro et al. | |
| 5,814,516 A | 9/1998 | Vo-Dinh | |
| 5,824,477 A | 10/1998 | Stanley | |
| 5,824,557 A | 10/1998 | Burke et al. | |
| 5,846,729 A | 12/1998 | Wu et al. | |
| 5,861,124 A | 1/1999 | Hosoi et al. | |
| 5,874,213 A * | 2/1999 | Cummins et al. ............... 435/6 |
| 5,874,555 A | 2/1999 | Dervan et al. | |
| 5,888,739 A | 3/1999 | Pitner et al. | |
| 5,912,332 A | 6/1999 | Agrawal et al. | |
| 5,948,897 A | 9/1999 | Sen et al. | |
| 6,013,442 A | 1/2000 | Kolesar et al. | |
| 6,017,709 A | 1/2000 | Hardin et al. | |
| 6,027,880 A | 2/2000 | Cronin et al. | |
| 6,046,004 A | 4/2000 | Wu et al. | |
| 6,048,690 A | 4/2000 | Heller et al. | |
| 6,051,380 A | 4/2000 | Sosnowski et al. | |
| 6,060,242 A | 5/2000 | Nie et al. | |
| 6,071,699 A * | 6/2000 | Meade et al. ............... 435/6 |
| 6,107,078 A | 8/2000 | Keese et al. | |
| 6,117,657 A | 9/2000 | Usman et al. | |
| 6,251,591 B1 | 6/2001 | Wu et al. | |
| 6,255,050 B1 | 7/2001 | Nie et al. | |
| 6,255,469 B1 | 7/2001 | Seeman et al. | |
| 6,265,170 B1 * | 7/2001 | Picard et al. ............... 435/6 |

(Continued)

FOREIGN PATENT DOCUMENTS

GB   2333359 A   7/1999

(Continued)

OTHER PUBLICATIONS

Blackburn et al "Electrochemiluminescence detection for development of immunoassays and dna probe assays for clinical diagnostics" Clinical Chemistry, 1991, 37(9): 1534-1539.*

(Continued)

*Primary Examiner*—BJ Forman
(74) *Attorney, Agent, or Firm*—Caesar, Rivise, Bernstein, Cohen & Pokotilow, Ltd.

(57) ABSTRACT

A method for homogeneously assaying biopolymer bonding includes obtaining signals from a test sample before, during and/or after the application of stimulus to the test sample and correlating the signals. The signals, whose magnitude correlate with binding affinity, can be, for example, electrical conductance and/or fluorescent intensity. The stimulus can be, for example, electric voltage and/or laser radiation. Preferably, different types of signals are measured and compared so as to enhance the reliability of the assay.

34 Claims, 8 Drawing Sheets

U.S. PATENT DOCUMENTS

| | | | |
|---|---|---|---|
| 6,287,772 | B1 | 9/2001 | Stefano et al. |
| 6,391,624 | B1 * | 5/2002 | Megerle ............... 435/287.2 |
| 6,403,313 | B1 | 6/2002 | Daksis et al. |
| 6,420,115 | B1 | 7/2002 | Erikson et al. |
| 6,426,407 | B1 * | 7/2002 | Fresco et al. ............... 536/22.1 |
| 6,613,524 | B1 | 9/2003 | Erikson |
| 6,656,692 | B2 * | 12/2003 | Erikson et al. ............... 435/6 |
| 6,664,071 | B1 | 12/2003 | Windhab et al. |
| 6,924,108 | B2 * | 8/2005 | Erikson et al. ............... 435/6 |
| 2002/0094531 | A1 * | 7/2002 | Zenhausern ............... 435/6 |
| 2002/0137056 | A1 | 9/2002 | Windhab et al. |

FOREIGN PATENT DOCUMENTS

| | | |
|---|---|---|
| GB | 2338301 A | 12/1999 |
| WO | WO 95/01370 A1 | 1/1995 |
| WO | WO 97/45539 A1 | 12/1997 |
| WO | WO 98/35012 A2 | 8/1998 |
| WO | WO 98/35012 A3 | 8/1998 |
| WO | WO 99/67628 A1 | 12/1999 |
| WO | WO 00/20633 A1 | 4/2000 |
| WO | WO 00 75792 | 12/2000 |

OTHER PUBLICATIONS

U.S. Appl. No. 09/468,679, Daksis et al.
U.S. Appl. No. 09/613,263, Erikson et al.
U.S. Appl. No. 09/664,827, Erikson et al.
U.S. Appl. No. 09/713,177, Erikson et al.
U.S. Appl. No. 09/885,731, Eriskon et al.
U.S. Appl. No. 09/909,496, Erikson et al.
Sturm et al., *Genes & Development*, 2:1582-1599 (1988).
Tomac et al., 118 *J. Am. Chem. Soc.* 5544-5552 (1996).
Watson, James, "A Personal Account of the Discovery of the Structure of DNA," (1968).
Williamson et al., *Cell* 59:871-880 (Dec. 1, 1989).
Wilson et al., *Cell*, 74:115-125 (Jul. 16, 1993).
Zhurkin et al., *J. Mol. Biol.*, vol. 239, 181-200 (1994).
Johansen and Jacobsen, *J Biomol Struct Dyn*, 16(2):205-22 (Oct. 1998) (Abstract).
Kadonaga et al., *Cell*, 51:1079-1090 (Dec. 24, 1987).
Kukreti et al, 25 *Nucleic Acids Research* 4264-4270 (1997).
Marsh et al., *Nucleic Acids Research*, 23:696-700 (1995).
Marsh et al., *Biochemistry* 33:10718-10724 (1994).
Mazumder et al., *Biochemistry* 35:13762-13771 (1996).
Sen et al., *Nature* 334:364-366 (1988).
Sen et al., *Biochemistry* 31:65-70 (1992).
Abstract of JP 5237000, Yoshitami (Sep. 17, 1993).
Baran et al., *Nucleic Acids Research* 25:297-303 (1997).
Bohmann et al., *Science*, 238:1386-1392 (Dec. 1987).
Carlsson et al., 380 *Nature* 207 (Mar. 21, 1996).
Chan et al., *J. Mol. Med.* 75 Issue 4:267-282 (1997).
Dalrymple et al., *Nucleic Acids Research*, vol. 13, No. 21, pp. 7865-7879 (1985).
Durland et al., *Biochemistry*, 30:9246-9255 (1991).
Egholm et al., 365 *Nature* 566 (Oct. 7, 1993).
Floris et al., 260 *Eur. J. Biochem.* 801-809 (1999).
Hill et al., *Methods in Enzymology*, 278:390-416 (1997).
Khrapko et al., " Identification of point mutations in mixtures by capillary electrophoresis hybridization," *Nucleic Acid Research*, vol. 26, No. 4, pp. 5738-5740 (1998).
Cheng et al., "Preparation and hybridization analysis of DNA/RNA from *E. coli* on microfabricated bioelectronic chips," *Nature Biotechnology*, vol. 16, pp. 541-548 (1998).

\* cited by examiner

Figure 1A (1V; antiparallel PNA probe)
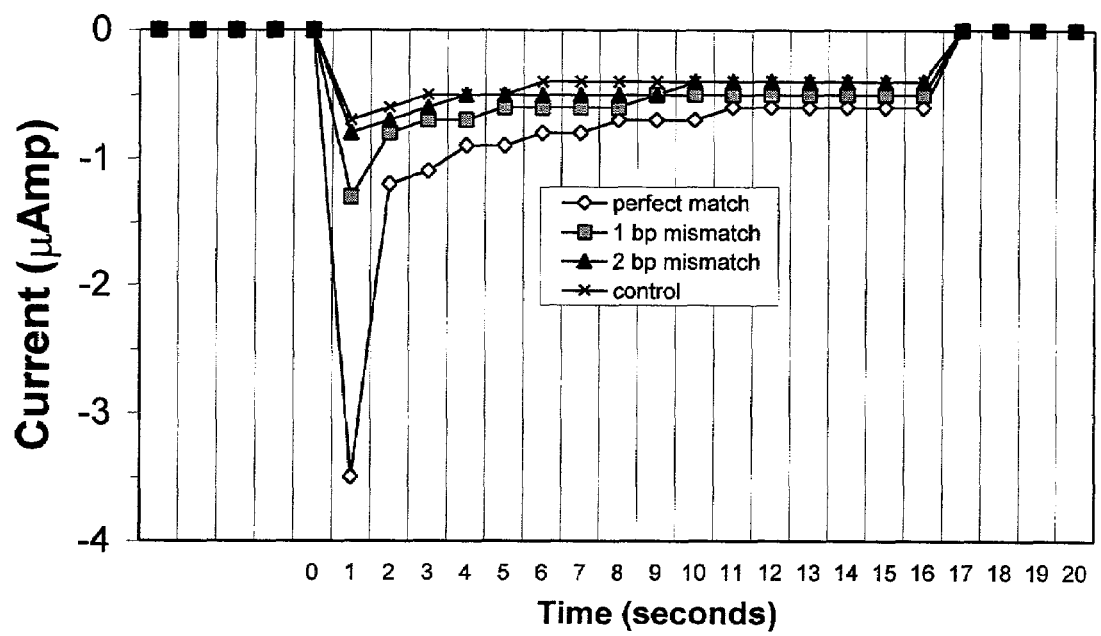
Figure 1B (5V; antiparallel PNA probe)
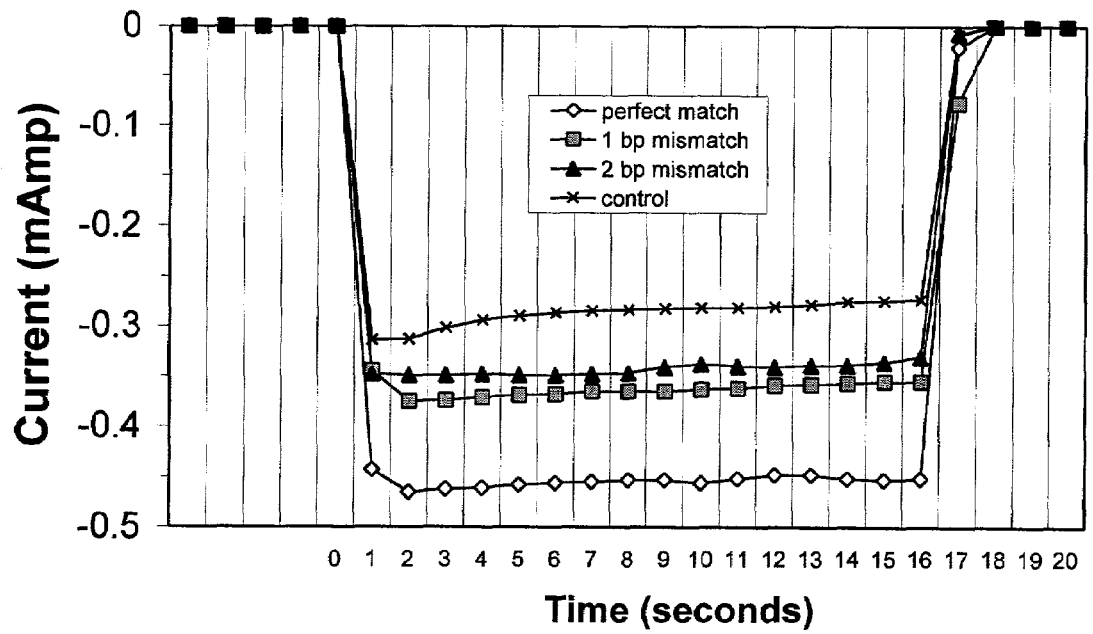

Figure 1C (1V; antiparallel PNA probe)
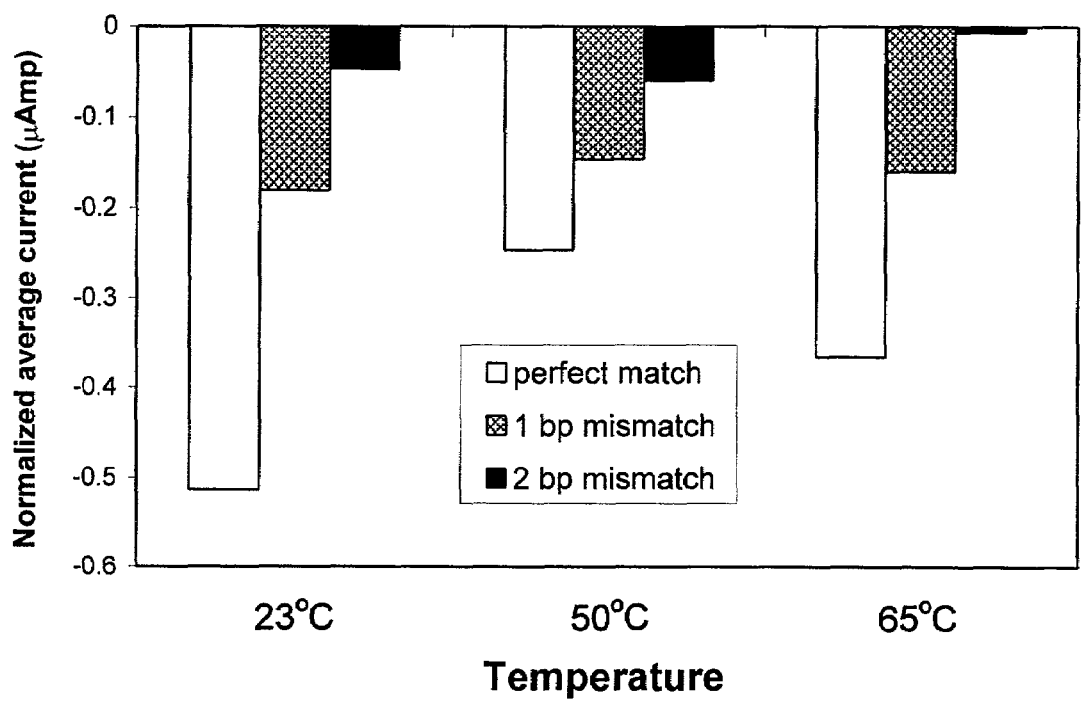
Figure 1D (5V; antiparallel PNA probe)
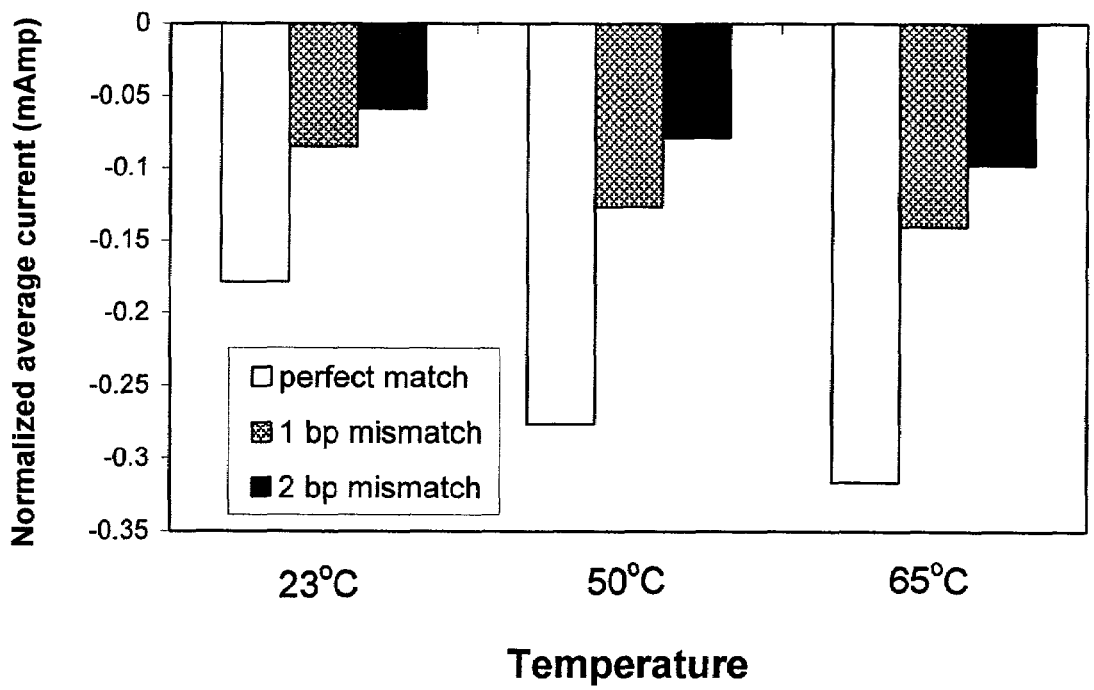

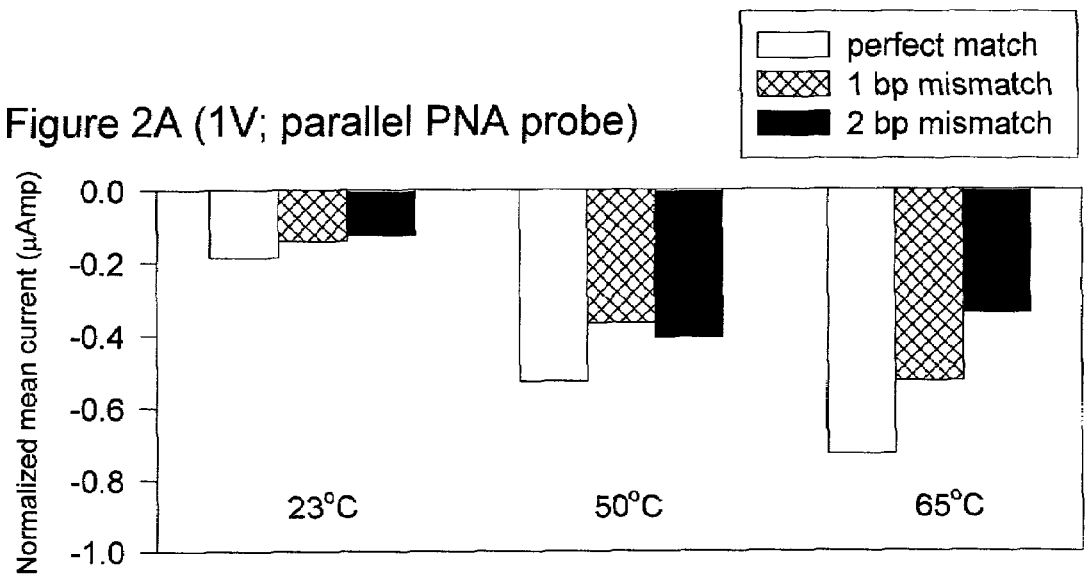
Figure 2A (1V; parallel PNA probe)
Figure 2B (5V; parallel PNA probe)
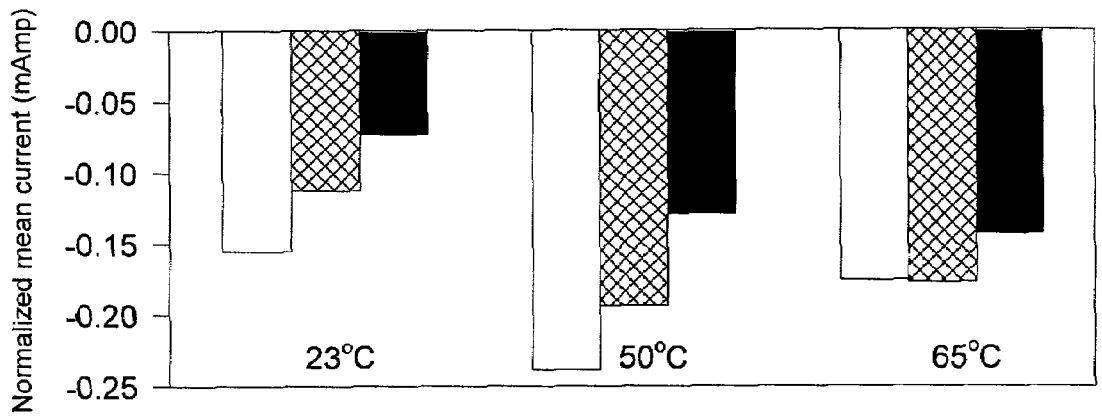
Figure 2C (5V; parallel PNA probe; 65°C treatment)
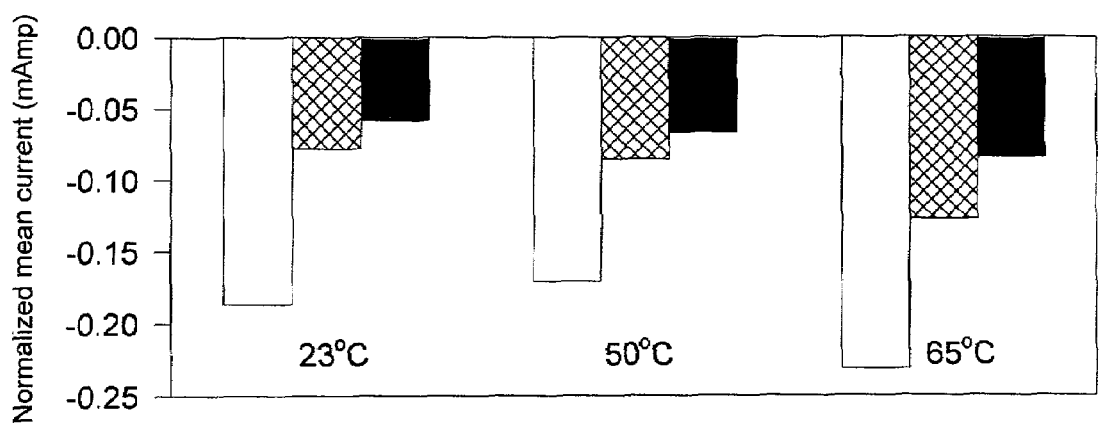

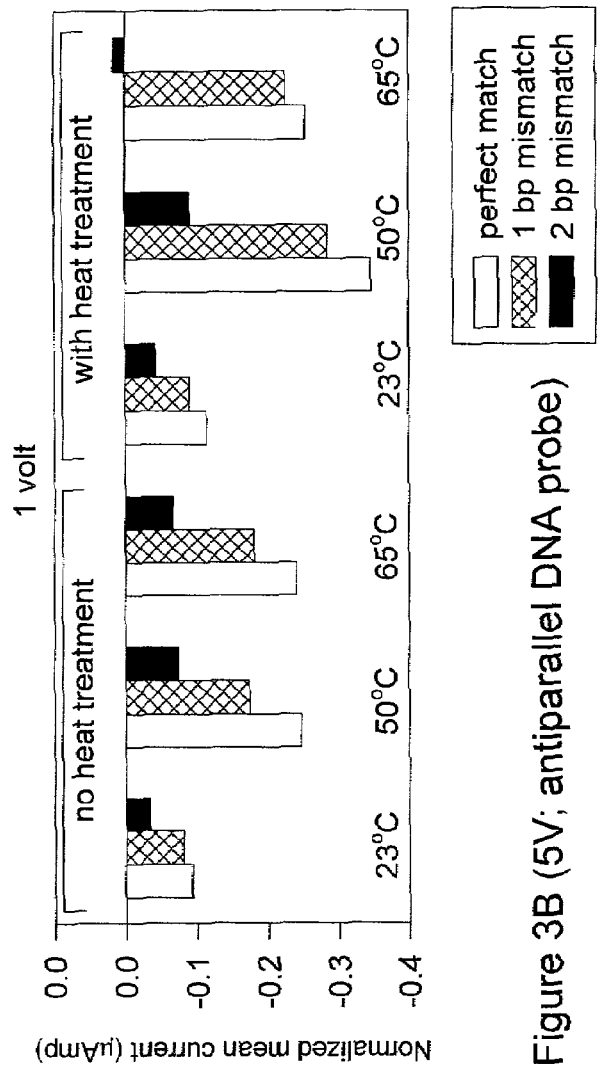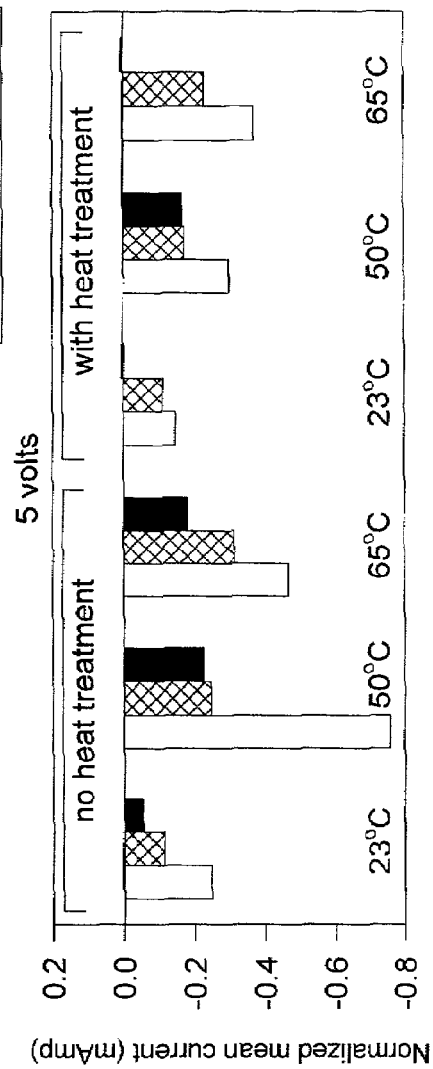
Figure 3A (1V; antiparallel DNA probe)
Figure 3B (5V; antiparallel DNA probe)

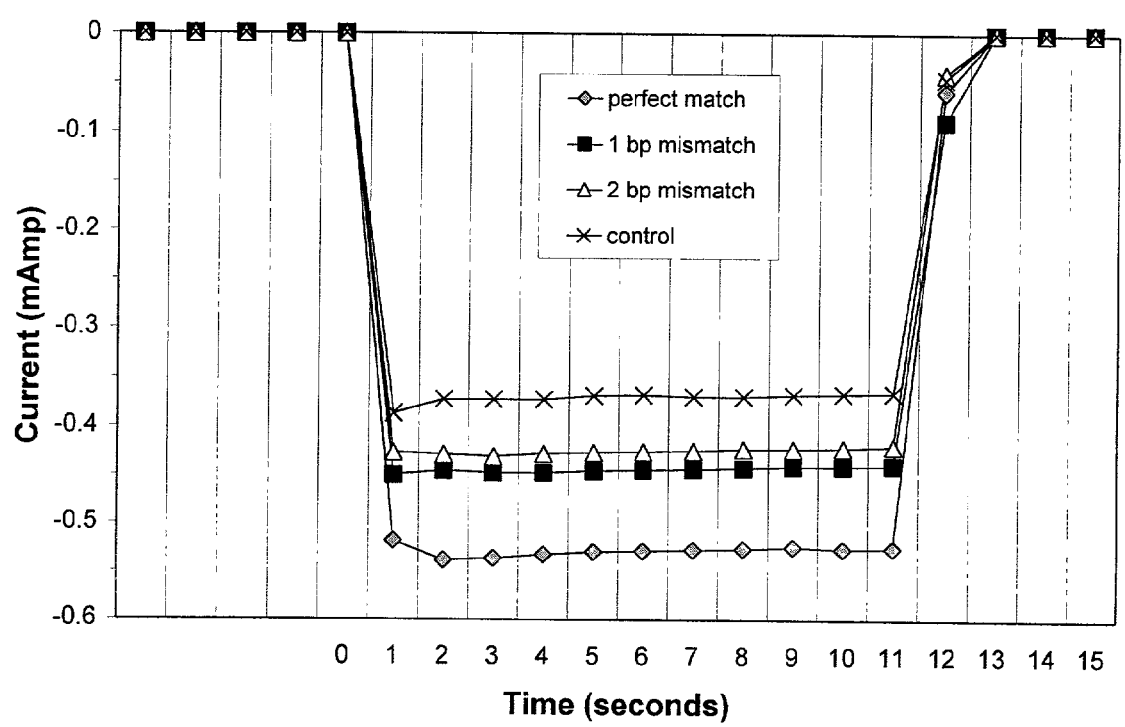
Figure 4 (5V; DNA probe with attached acridine)

Figure 5A (PNA:DNA perfect match; 65°C)
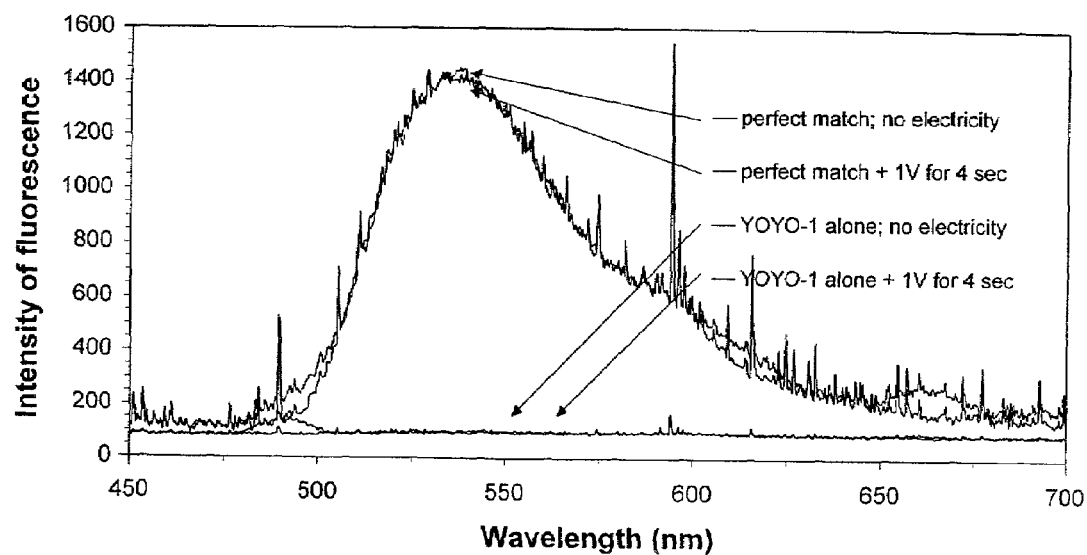
Figure 5B (PNA:DNA 1bp mismatch; 65°C)
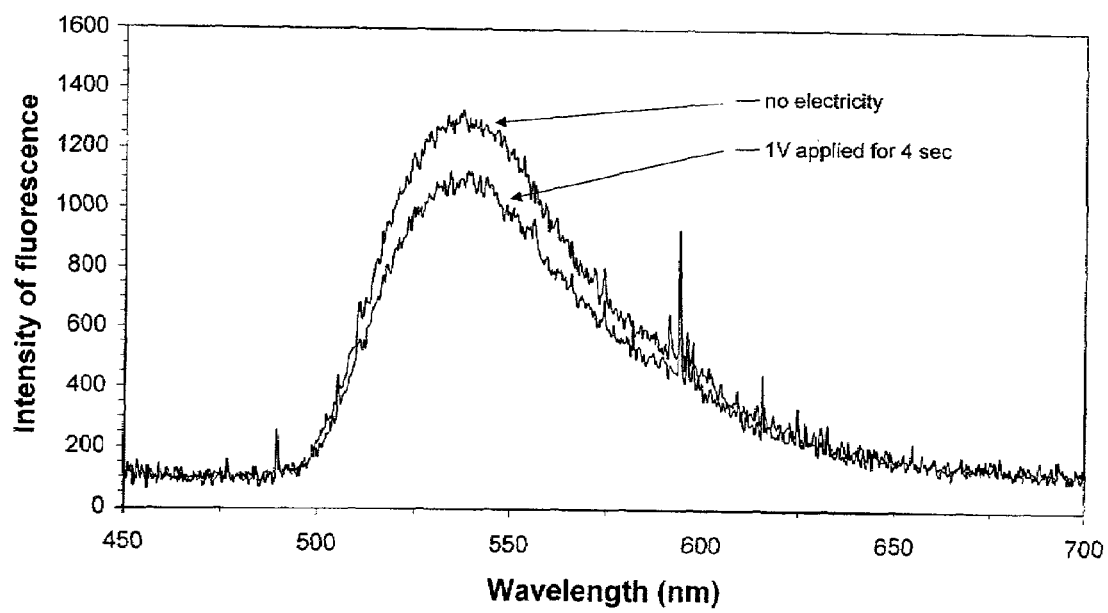

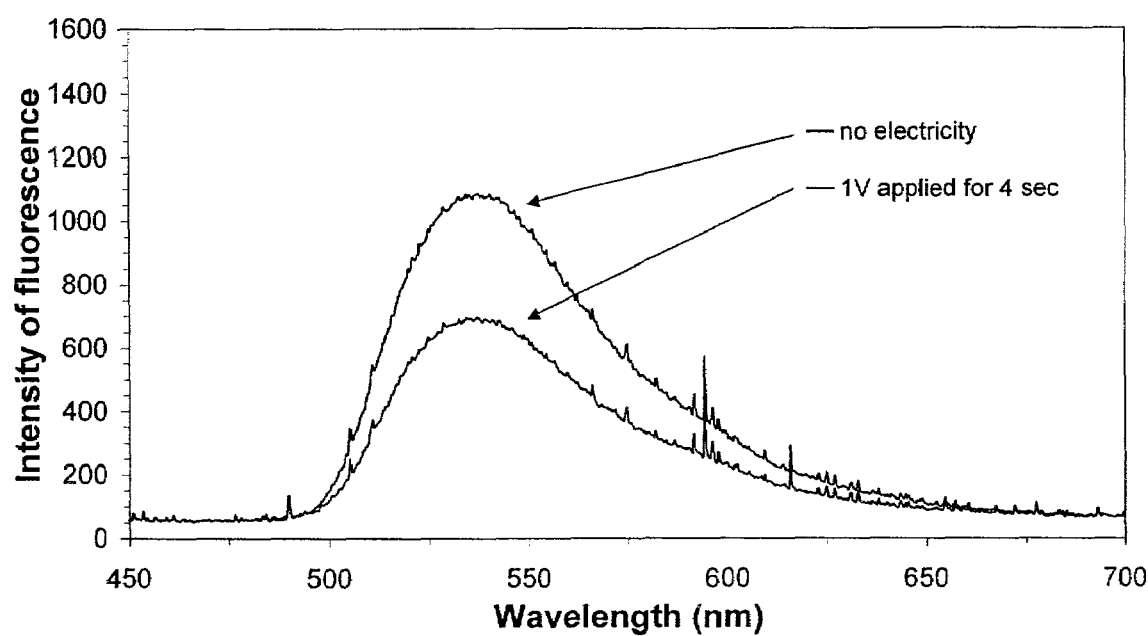
Figure 5C (PNA:DNA 2bp mismatch; 65°C)

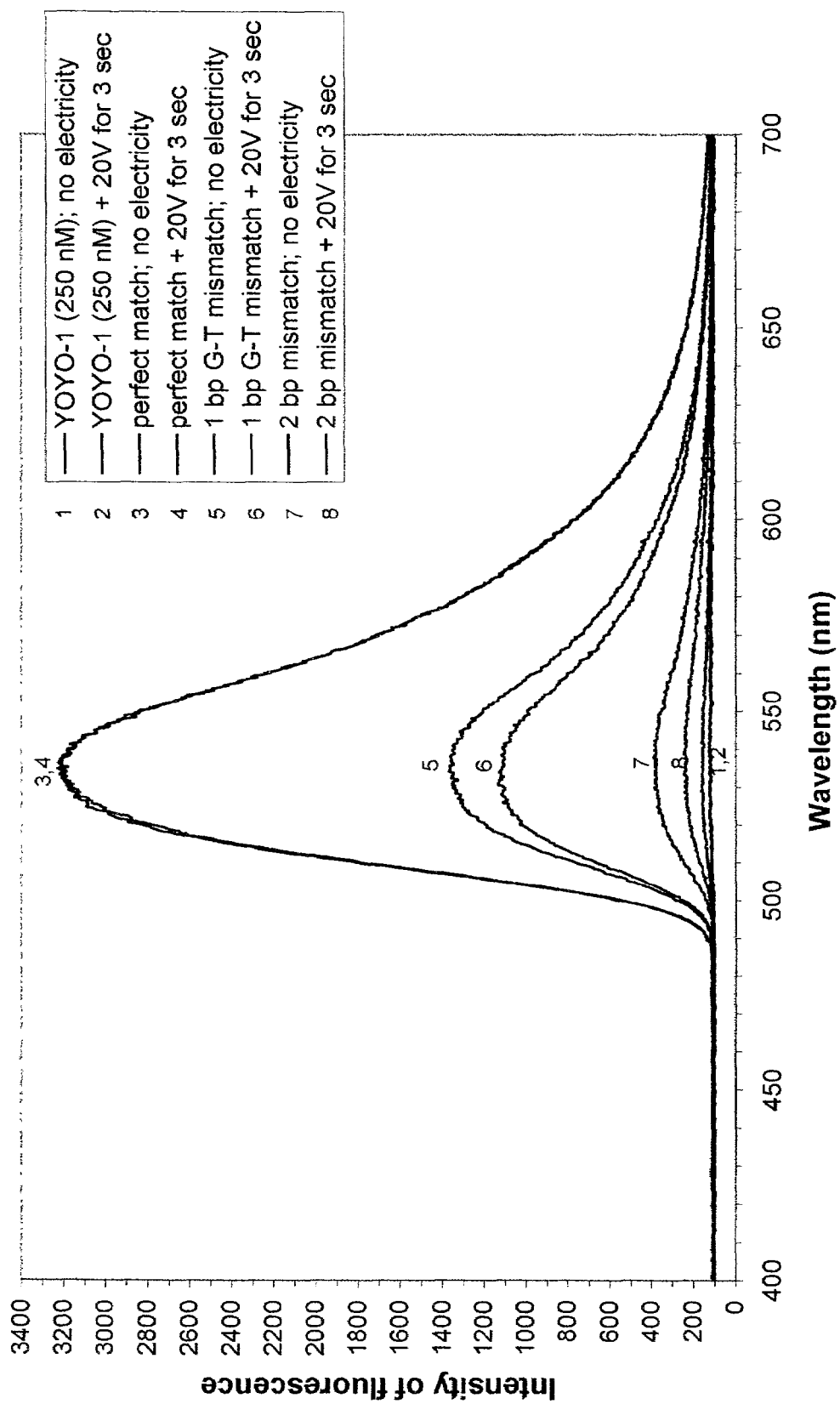

SEQUENCE LISTING

<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 1
tggcaccatt aaagaaaata tcatctttgg tgtttcctat gatgaatata            50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 2
tggcaccatt aaagaaaata tcgtctttgg tgtttcctat gatgaatata            50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 3
tggcaccatt aaagaaaata tactctttgg tgtttcctat gatgaatata            50

<210> SEQ ID NO 4
<211> LENGTH: 15

```
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 4
atatcatctt tggtg                                                        15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 5
atatcatcta tggtg                                                        15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 6
atatcggctt tggtg                                                        15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 7
ataccatatt tagtg                                                        15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: ssDNA probe
      wherein the 3' end of each base is covalently bonded to a lysine
      N-terminal leaving a free carboxyl group

<400> SEQUENCE: 8
caccaaagat gatat                                                        15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: ssDNA probe
      wherein the 3' end of each base is covalently bonded to a lysine
      N-terminal leaving a free carboxyl group

<400> SEQUENCE: 9
tatagtagaa accac
```

HOMOGENEOUS ASSAY OF BIOPOLYMER BINDING BY MEANS OF MULTIPLE MEASUREMENTS UNDER VARIED CONDITIONS

CROSS REFERENCE TO RELATED APPLICATIONS

This application is a continuation-in-part of U.S. patent application Ser. No. 09/490,273, filed Jan. 24, 2000 now U.S. Pat. No. 6,265,170.

BACKGROUND OF THE INVENTION

1. Field of Invention

The invention relates to methods of assaying biopolymer binding, and more particularly to methods of assaying binding of probes and targets containing nucleobases and/or amino acids.

2. Description of Related Art

It has been understood for a number of years that biological molecules can be isolated and characterized through the application of an electric field to a sample.

Electrophoresis is perhaps the most well-known example of an isolation and characterization technique based on the influence of electric fields on biological molecules. In gel electrophoresis, a uniform matrix or gel is formed of, for example, polyacrylamide, to which an electric field is applied. Mixtures applied to one end of the gel will migrate through the gel according to their size and interaction with the electric field. Mobility is dependent upon the unique characteristics of the substance such as conformation, size and charge. Mobilities can be influenced by altering pore sizes of the gel, such as by formation of a concentration or pH gradient, or by altering the composition of the buffer (pH, SDS, DOC, glycine, salt). One- and two-dimensional gel electrophoresis are fairly routine procedures in most research laboratories. Target substances can be purified by passage through and/or physical extraction from the gel.

A more recently developed process in which an electric field is applied to a biological sample is disclosed in U.S. Pat. No. 5,824,477 to Stanley. The Stanley patent discloses a process for detecting the presence or absence of a predetermined nucleic acid sequence in a sample. The process comprises: (a) denaturing a sample double-stranded nucleic acid by means of a voltage applied to the sample in a solution by means of an electrode; (b) hybridizing the denatured nucleic acid with an oligonucleotide probe for the sequence; and (c) determining whether the hybridization has occurred. The Stanley patent discloses the application of an electric field to the sample to be assayed for the limited purpose of denaturing the target sequence.

A more well-known type of hybridization assay is based on the use of fluorescent marking agents. In their most basic form, fluorescent intensity-based assays have typically comprised contacting a target with a fluorophore-containing probe, removing any unbound probe from bound probe, and detecting fluorescence in the washed sample. Homogeneous assays improve upon such basic assays, in that the former do not require a washing step or the provision of a non-liquid phase support.

Some assays have employed intercalating fluorophores to detect nucleic acid hybridization, based on the ability of such fluorophores to bind between strands of nucleic acid in a hybridization complex.

For example, U.S. Pat. No. 5,824,557 to Burke et al. discloses a method and kit for detecting and quantitating nucleic acid molecules. A preferred embodiment relies on the intercalation of a dye into a double-stranded nucleic acid helix or single-stranded nucleic acid. The dye fluoresces after intercalation and the intensity is a direct measurement of the amount of nucleic acid present in the sample. While the method of Burke et al. is purported to be useful for measuring the amount of nucleic acid in a sample, the non-specific binding between intercalator and nucleic acid upon which the method is based renders the method impractical for detecting specific binding, particularly under conditions where non-target nucleic acid duplexes are present.

U.S. Pat. No. 5,814,447 to Ishiguro et al. discloses an assay which is purported to improve upon assays that rely on non-specific interaction between intercalating agents and nucleic acid duplexes, such as Burke et al. and an earlier assay described by Ishiguro et al. in Japanese Patent Public Disclosure No. 237000/1993. The earlier development comprised adding an intercalating fluorochrome having a tendency to exhibit increased intensity of fluorescence when intercalated to a sample solution before a specific region of a target nucleic acid was amplified by PCR, and measuring the intensity of fluorescence from the reaction solution at given time intervals to detect and quantitate the target nucleic acid before amplification. The '447 patent attempted to improve upon the earlier development by providing an assay having improved specificity, characterized in that the probe is a single-stranded oligonucleotide labeled with an intercalating fluorochrome which is to be intercalated into a complementary binding portion between a target nucleic acid and a single-stranded oligonucleotide probe.

In the ongoing search for more sensitive, accurate and rapid assay techniques, one research group developed an assay comprising analyzing the effects of an electric field on the fluorescent intensity of nucleic acid hybridization duplexes. See U.S. patent application Ser. No. 08/807,901, filed Feb. 27, 1997 and U.S. Pat. No. 6,060,242. The researchers indicated that the fluorescent intensity of a one base-pair mismatched duplex differed from that of a perfectly matched duplex. Thus, the applications purport to disclose a method for detecting a nucleotide sequence, wherein an electric field is applied to a liquid medium prior to or concurrently with a detecting step, and a change in an intensity of a fluorescent emission as a function of the electric field is detected as an indication of whether the probe is hybridized to a completely complementary nucleotide sequence or an incompletely complementary nucleotide sequence.

Despite the foregoing developments, a need has continued to exist in the art for a simple, highly sensitive, effective and rapid method for analyzing interaction between nucleic acids and/or nucleic acid analogs.

All references cited herein are incorporated herein by reference in their entireties.

BRIEF SUMMARY OF THE INVENTION

The invention provides a method for assaying sequence-specific hybridization, which comprises:

providing a target comprising at least one target biopolymer sequence;

providing a probe comprising at least one probe biopolymer sequence;

adding the probe and the target to a binding medium to provide a test sample;

applying a first stimulus to the test sample to provide a first stimulated test sample;

detecting a first signal from the first stimulated test sample, wherein the first signal is correlated with a binding affinity between the probe and the target;

applying a second stimulus to the first stimulated test sample to provide a second stimulated test sample;

detecting a second signal from the second stimulated test sample, wherein the second signal is correlated with the binding affinity between the probe and the target; and comparing the first signal and the second signal to accomplish the assaying;

wherein at least one label is provided in the test sample, and the first stimulus, the second stimulus, the first signal and the second signal are electromagnetic radiation, provided that when the first stimulus and the second stimulus are photonic radiation, an intermediate electronic stimulus is applied to the test sample after the first stimulus and before the second stimulus, and when the first stimulus and the second stimulus are electronic radiation, the first signal and the second signal are electric current.

Also provided is a method for assaying sequence-specific hybridization, the method comprising:

providing a target;

providing a probe, wherein at least one of the probe and the target comprises at least one biopolymer sequence;

adding the probe and the target to a binding medium to provide a test sample;

applying a first stimulus to the test sample to provide a first stimulated test sample;

detecting a first signal from the first stimulated test sample, wherein the first signal is correlated with a binding affinity between the probe and the target;

applying a second stimulus to the first stimulated test sample to provide a second stimulated test sample;

detecting a second signal from the second stimulated test sample, wherein the second signal is correlated with the binding affinity between the probe and the target; and comparing the first signal and the second signal to accomplish the assaying;

wherein at least one label is provided in the test sample, and the first stimulus, the second stimulus, the first signal and the second signal are electromagnetic radiation, provided that when the first stimulus and the second stimulus are photonic radiation, an intermediate electronic stimulus is applied to the test sample after the first stimulus and before the second stimulus, and when the first stimulus and the second stimulus are electronic radiation, the first signal and the second signal are electric current.

BRIEF DESCRIPTION OF SEVERAL VIEWS OF THE DRAWINGS

The invention will be described in conjunction with the following drawings in which like reference numerals designate like elements and wherein:

FIGS. 1A and 1B are graphs of current as a function of time and complementarity;

FIGS. 1C and 1D are graphs of current as a function of temperature and complementarity;

FIGS. 2A, 2B, 2C, 3A and 3B are graphs of current as a function of temperature, complementarity and additional factors;

FIG. 4 is a graph of current as a function of time and complementarity; and

FIGS. 5A, 5B, 5C and 6 are fluorescent intensity spectra.

DETAILED DESCRIPTION OF THE INVENTION

The invention provides a rapid, sensitive, environmentally friendly, and safe method for assaying binding between a target and a probe, wherein the target comprises a nucleic acid sequence or a nucleic acid analog sequence and the probe comprises a nucleic acid sequence or a nucleic acid analog sequence. The assay of the invention is also suitable for assaying binding between a target and a probe, wherein the target and/or the probe comprises an amino acid sequence. Thus, the invention is suitable for assaying binding of biopolymers, which as used herein, means a sequence containing at least two amino acids, amino acid analogs, nucleic acids, nucleic acid analogs and/or combinations thereof.

Unlike certain prior art assays, the invention not only detects the presence of specific binding, but also provides qualitative and quantitative information regarding the nature of binding between a probe and target. Thus, in embodiments comprising nucleobase to nucleobase binding assays, the invention enables the practitioner to distinguish among a perfect match, a one base pair mismatch, a two base pair mismatch, a three base pair mismatch, a one base pair deletion, a two base pair deletion and a three base pair deletion.

Embodiments of the invention comprise calibrating the measured signal (e.g., electric current and/or fluorescent intensity) for a first probe-target mixture against the same type of signal exhibited by other probes combined with the same target, wherein each of the other probes differs from the first probe by at least one base.

In certain embodiments, a low voltage is applied to the sample prior to or concurrent with measuring said signal. Generally, the voltage is selected such that it is high enough to destabilize imperfectly matched hybridization partners but not so high as to destabilize perfectly matched hybridization partners. In certain preferred embodiments, the voltage is about 1V to about 20V.

A calibration curve can be generated, wherein the magnitude of the measured signal (e.g., electric current and/or fluorescent intensity) is a function of the binding affinity between the target and probe. As the binding affinity between the target and a plurality of different probes varies with the number of mismatched bases in nucleobase-nucleobase assays, the nature of the mismatch (A-G vs. A-C vs. T-G vs. T-C, etc.), the location of the mismatch(es) within the hybridization complex, etc., the assay of the invention can be used to sequence the target.

The signal measured can be, e.g., electrical conductance. In such embodiments, the binding affinity between the probe and target is directly correlated with the magnitude of the signal. That is, the electrical conductance increases along with the extent of matching between the probe and target, preferably over a range inclusive of 0-2 mismatches and/or deletions, more preferably over a range inclusive of 0-3 mismatches and/or deletions.

In other embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Thus, the fluorescent intensity generated by intercalating agents is directly correlated with probe-target binding affinity, whereas the intensity of embodiments employing non-intercalating fluorophores covalently bound to the probe is inversely correlated with probe-target binding affinity. The fluorescent intensity increases (or decreases for non-intercalators) along with the extent of matching between the probe and target, preferably over a range inclusive of 0-2 mismatches and/or deletions, more preferably over a range inclusive of 0-3 mismatches and/or deletions.

Although the inventors have previously disclosed the advantages of fluorescent intensity assays for analyzing hybridization of nucleobase-containing sequences (see U.S. patent application Ser. No. 09/468,679, filed Dec. 21, 1999) and the advantages of fluorescent intensity assays for analyzing peptide:nucleic acid binding (see U.S. patent application Ser. No. 09/224,505, filed Dec. 31, 1998) and peptide:peptide binding (see U.S. patent application Ser. No. 09/344,525, filed Jun. 25, 1999), the application of an electric field to the sample appears to increase the resolution of the assay, as shown in Example 6 below.

Moreover, in particularly preferred embodiments of the invention, the assay comprises measuring at least two signals of the sample. The first signal is preferably fluorescent intensity and the second signal is preferably selected from several electrical conductance measurements (or vice versa).

In the preferred multiple measurement embodiments, the first signal can be the same as or different from the second signal. When the first and second signals measured are the same, the second signal can be calibrated against the first signal and/or against the same reference signal(s) used to calibrate the first signal. In addition, at least one condition-altering stimulus is preferably applied to the test sample after the first signal is measured and before the second signal is measured. The stimulus is preferably sufficient to measurably change binding, as indicated by at least one signal. In nucleobase-nucleobase binding assays of the invention, the stimulus is preferably sufficient to significantly affect imperfectly complementary hybridization between the probe and the target and insufficient to significantly affect perfectly complementary hybridization between the probe and the target.

In certain embodiments of the invention, at least one stimulus is applied once or a plurality of times. The stimulus can be continuously applied or non-continuously applied. The stimulus can be applied before, during and/or after the detection of signal detection.

Suitable stimuli can be, e.g., photonic radiation (such as laser light) and/or electronic. The signals detected can be, e.g., photonic and/or electronic as well.

For example, in a particularly preferred embodiment of the invention, the first signal measured is pre-electrification fluorescent intensity (i.e., intensity measured before a condition-altering voltage is applied to the test sample) and the second signal measured is post-electrification fluorescent intensity (i.e., intensity measured during or after the condition-altering voltage has been applied to the test sample)

The additional measurements in the foregoing embodiments increase the reliability of the assay and enable immediately retesting suspect results. Inconsistent results achieved by the at least two measurements will typically warrant retesting.

The invention enables quantifying the binding affinity between probe and target. Such information can be valuable for a variety of uses, including designing antisense drugs with optimized binding characteristics.

Unlike prior art methods, the assay of the invention is preferably homogeneous. The assay can be conducted without separating the probe-target complex from the free probe and target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor requirements to be rapidly determined.

The assay can be conducted in e.g., a solution within a well, on an impermeable surface or on a biochip.

Moreover, the inventive assay is preferably conducted without providing a signal quenching agent on the target or on the probe.

Preferred embodiments of the invention specifically detect triplex and/or quadruplex hybridization between the probe and the double-stranded target, thus obviating the need to denature the target. Triplex and quadruplex formation and/or stabilization is enhanced by the presence of an intercalating agent in the sample being tested. See, e.g., U.S. patent application Ser. No. 09/885,731, filed Jun. 20, 2001, and the U.S. Patent Application Ser. No. 09/909,496, entitled "PARALLEL OR ANTIPARALLEL, HOMOLOGOUS OR COMPLEMENTARY BINDING OF NUCLEIC ACIDS OR ANALOGUES THEREOF TO FORM DUPLEX, TRIPLEX OR QUADRUPLEX COMPLEXES", filed Jul. 20, 2001.

Complexes of the invention preferably do not rely on Hoogsteen bonding or G-G quartets for maintenance of the complex structure, although Hoogsteen bonding and/or G-G quartets may be present. That is, complexes of the invention are preferably substantially free of Hoogsteen bonding, and substantially free of G-G quartets.

Suitable nucleobase-containing probes for use in the inventive assay include, e.g., ssDNA, RNA, PNA and other nucleic acid analogs having uncharged or partially-charged backbones. Although antiparallel probes are preferred in certain embodiments, probes can also be parallel. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 6 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

Suitable amino acid-containing probes can comprise a single amino acid, single amino acid analog, a peptide-like analog, peptidoid, peptidomimetic, peptide, dipeptide, tripeptide, polypeptide, protein or a multi-protein complex.

The invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments of the invention wherein the target comprises amino acids, the target preferably comprises a peptide sequence or a peptide-like analog sequence, such as, e.g., a dipeptide, tripeptide, polypeptide, protein or a multi-protein complex. More preferably, the target is a protein having at least one receptor site for the probe.

In embodiments of the invention wherein the target comprises nucleobases, the targets are preferably 8 to 3.3×109 base pairs long, and can be single or double-stranded sequences of nucleic acids and/or analogs thereof.

It is preferred that the probe and target be unlabeled, but in alternative embodiments, there is an intercalating agent covalently bound to the probe. In such embodiments, the intercalating agent is preferably bound to the probe at either end.

In other embodiments, the intercalating agent is not covalently bound to the probe, although it can insert itself between the probe and target during the assay, in a sense bonding to the probe in a non-covalent fashion.

Preferred intercalating agents for use in the invention include, e.g., YOYO-1, TOTO-1, ethidium bromide, ethidium homodimer-1, ethidium homodimer-2 and acridine. In general, the intercalating agent is a moiety that is able to intercalate between strands of a duplex, triplex and/or a quadruplex nucleic acid complex. In preferred embodiments, the intercalating agent (or a component thereof) is essentially non-fluorescent in the absence of nucleic acids and fluoresces when intercalated and excited by radiation of an appropriate wavelength, exhibiting a 100-fold to 10,000-fold enhancement of fluorescence when intercalated within a duplex or triplex nucleic acid complex.

In alternative embodiments, the intercalating agent may exhibit a shift in fluorescent wavelength upon intercalation and excitation by radiation of an appropriate wavelength. The exact fluorescent wavelength may depend on the structure of the nucleic acid that is intercalated, for example, DNA vs. RNA, duplex vs. triplex, etc.

The excitation wavelength is selected (by routine experimentation and/or conventional knowledge) to correspond to this excitation maximum for the fluorophore being used, and is preferably 200 to 1000 nm. Intercalating agents are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The inventive assay is extremely sensitive, thereby obviating the need to conduct PCR amplification of the target. For example, in at least the fluorescent intensity embodiments, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^{-9}$ M, preferably at a concentration of not more than $5 \times 10^{-10}$ M.

Conductivity measurements can distinguish samples having as little as about 1 pmole of probe and 1 pmole of target in 40 microliters. Decreasing the sample volume would permit the use of even smaller amounts of probe and target.

It should go without saying that the foregoing values are not intended to suggest that the method cannot detect higher concentrations.

A wide range of intercalator concentrations are tolerated at each concentration of probe and target tested. For example, when $5 \times 10^{-10}$ M probe and $5 \times 10^{-10}$ M target are hybridized, the optimal concentration of the intercalator YOYO-1 ranges from 25 nM to 2.5 nM. At a $5 \times 10^{-8}$ M concentration of both probe and target, the preferred YOYO-1 concentration range is 1000 nM to 100 nM.

The assay is sufficiently sensitive to distinguish a one base-pair mismatched probe-target complex from a two base-pair mismatched probe-target complex, and preferably a two base-pair mismatched probe-target complex from a three base-pair mismatched probe-target complex. Of course, the assay is sufficiently sensitive to distinguish a perfectly matched probe-target complex from any of the above mismatched complexes.

The binding medium can be any conventional medium known to be suitable for preserving nucleotides and/or proteins. See, e.g., Sambrook et al., "Molecular Cloning: A Lab Manual," Vol. 2 (1989). For example, the liquid medium can comprise nucleotides, water, buffers and standard salt concentrations.

Hybridization between complementary bases occurs under a wide variety of conditions having variations in temperature, salt concentration, electrostatic strength, and buffer composition. Examples of these conditions and methods for applying them are known in the art.

It is preferred that hybridization complexes be formed at a temperature of about 15° C. to about 25° C. for about 1 minute to about 5 minutes. Longer reaction times are not required, but incubation for several hours will not adversely affect the hybridization complexes.

It is possible (although unnecessary, particularly for embodiments containing an intercalating agent) to facilitate hybridization in solution by using certain reagents. Preferred examples of these reagents include single stranded binding proteins such as Rec A protein, T4 gene 32 protein, *E. coli* single stranded binding protein, major or minor nucleic acid groove binding proteins, divalent ions, polyvalent ions, viologen and intercalating substances such as ethidium bromide, actinomycin D, psoralen, and angelicin. Such facilitating reagents may prove useful in extreme operating conditions, for example, under abnormal pH levels or extremely high temperatures.

The inventive assay can be used to, e.g., identify accessible regions in folded nucleotide sequences, to determine the number of mismatched base pairs in a hybridization complex, and to map genomes.

In embodiments wherein fluorescent intensity is detected using an intercalating agent, intensity increases with increasing binding affinity between the probe and target. In embodiments wherein fluorescent intensity is detected using a non-intercalating fluorophore, intensity decreases as binding affinity increases between the probe and target. Regardless of whether the fluorophore intercalates or not, the instant method does not require the measurement of the polarization of fluorescence, unlike fluorescent anisotropy methods.

The invention will be illustrated in more detail with reference to the following Examples, but it should be understood that the present invention is not deemed to be limited thereto.

EXAMPLES

Example 1

Sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. Equimolar amounts of complementary oligonucleotides were denatured at 95° C. for 10 min and allowed to anneal gradually as the temperature cooled to 21° C. over 1.5 hours. Double stranded DNA (dsDNA) oligonucleotides were dissolved in ddH$_2$O at a concentration of 1 pmole/µl.

Sequence for the sense strand of the wild-type target DNA (SEQ ID NO: 1): 5'-TGG CAC CAT TAA AGA AAA TAT CAT CTT TGG TGT TTC CTA TGA TGA ATA TA-3'.

Sequence for the antisense strand of the wild-type target DNA (SEQ ID NO: 1): 5'-TAT ATT CAT CAT AGG AAA CAC CAA AGA TGA TAT TTT CTT TAA TGG TGC CA-3'.

The predicted melting temperature (T$_m$) of dsDNA (SEQ ID NO:1) is 65.2° C.

SEQ ID NO:2 was a 50-mer mutant dsDNA target sequence identical to wild-type target DNA (SEQ ID NO:1) except for a one base pair mutation (underlined) at amino acid position 507 at which the wild-type sequence CAT was changed to CGT.

Sequence for the sense strand of

SEQ ID NO: 2: 5'-TGG CAC CAT TAA AGA AAA TAT C<u>G</u>T CTT TGG TGT TTC CTA TGA TGA ATA TA-3'.

Sequence for the antisense strand of

SEQ ID NO: 2: 5'-TAT ATT CAT CAT AGG AAA CAC CAA AGA <u>C</u>GA TAT TTT CTT TAA TGG TGC CA-3'.

The predicted melting temperature (T$_m$) of dsDNA (SEQ ID NO:2) is 66.0° C.

SEQ ID NO:3 was a 50-mer mutant dsDNA target sequence identical to wild-type target DNA (SEQ ID NO:1) except for a consecutive two base pair mutation (underlined) at amino acid positions 506 and 507 at which the wild-type sequence CAT was changed to <u>ACT</u>.

Sequence for the sense strand of

SEQ ID NO: 3: 5'-TGG CAC CAT TAA AGA AAA TAT <u>ACT</u> CTT TGG TGT TTC CTA TGA TGA ATA TA-3'.

Sequence for the antisense strand of

SEQ ID NO: 3: 5'-TAT ATT CAT CAT AGG AAA CAC CAA AGA <u>GTA</u> TAT TTT CTT TAA TGG TGC CA-3'.

The predicted melting temperature (T$_m$) of dsDNA (SEQ ID NO:3) is 65.2° C.

The PNA probes used in the Examples were synthesized, HPLC purified and confirmed by mass spectroscopy by Commonwealth Biotechnologies, Inc. (Richmond, Va., USA). PNA probes were first dissolved in 0.1% TFA (trifluoroacetic acid) to a concentration of 10 mg/ml, and then diluted to 1 mg/ml by the addition of ddH$_2$O. Final PNA stock solutions were prepared in ddH$_2$O at a concentration of 1 pmole/µl.

Probe No. 1 was a 15-mer antiparallel PNA probe designed to be completely complementary to a 15 nucleotide segment of the sense strand of the 50-mer wild-type target DNA (SEQ ID NO:1), overlapping amino acid positions 505 to 510 (Nature 380, 207 (1996)). The probe had the following structure (SEQ ID NO:8):

5'-H-CAC CAA AGA TGA TAT-Lys-CONH$_2$-3'

The hybridization reaction mixture (80 µl) contained the following: 2 pmoles of target dsDNA, 2 pmoles of PNA probe, 0.5×TBE and 250 nM of the DNA intercalator YOYO-1 (Molecular Probes, Eugene, Oreg., USA). Samples were placed into a 3 mm quartz cuvette and were subjected to 1 or 5 volts DC (V) electrification for 15 seconds. The amperometric assay consisted of the monitoring of current while the voltage was being applied to the solution. A temperature probe was placed in each solution to measure temperature at the time of amperometric assessment. At 1 volt, a current peak was observed during the first 2 seconds of electrification. The current declined sharply over the following 13 seconds. Experiments applying 5 volts gave rise to currents that remained relatively stable over the entire electrification period (15 seconds).

A series of experiments were carried out where the conductance values were observed when no DNA or PNA was present (control), or when wild-type SEQ ID NO:1, mutant SEQ ID NO:2 or mutant SEQ ID NO:3 were reacted with antiparallel PNA Probe No. 1. FIGS. 1A and 1B plot the data obtained for conductance in the individual experiments. FIG. 1A displays the results of the application of 1V electrification and FIG. 1B the application of 5V. Double stranded DNA:PNA hybrid triplexes consisting of perfectly complementary sequences (SEQ ID NO:1+Probe No. 1) allowed maximum intercalation of YOYO-1, yielding the highest conductance values (depicted on the figures as negative current values) throughout the entire 15 seconds of 1V application. The normalized peak conductance for the triplex hybridization of the antiparallel PNA probe with a 1 bp mismatched dsDNA (SEQ ID NO:2+Probe No. 1) and with the 2 bp mismatched dsDNA (SEQ ID NO:3+Probe No. 1) were respectively 79% and 96% lower than that observed with the perfectly matched dsDNA:PNA triplex hybrid (SEQ ID NO: 1+Probe No. 1) during the first second of voltage application (FIG. 1A). Similar percent decreases in conductance between perfectly complementary triplexes and triplexes containing base pair mismatches were obtained when the conductance values over the entire 15 seconds of voltage application were averaged. In FIG. 1A the 1 bp and 2 bp mismatched dsDNA:PNA hybrids resulted in average conductance values that were 65% and 91% lower, respectively, than those for the perfectly matched dsDNA:PNA hybrid. All experiments expressed in FIG. 1A were carried out at room temperature (23° C.). As the degree of mismatch between the probe and the double stranded target increased, the level of intercalation by YOYO-1 diminished and the level of conductance decreased. These relationships were also observed when the experiments referred to above were repeated and a higher voltage (5V) was applied. During the 5V application the normalized average conductance values for the 1 bp mismatched dsDNA:PNA triplex (SEQ ID NO:2+Probe No. 1) and the 2 bp mismatched dsDNA:PNA triplex (SEQ ID NO:3+Probe No. 1) were respectively 52% and 67% lower than that observed for the perfectly matched dsDNA:PNA triplex (SEQ ID NO:3+Probe No. 1) (FIG. 1B). Experiments expressed in FIG. 1B were performed at room temperature (23° C.).

When the experiments were repeated with the temperature increased to 50° C. and 65° C., similar amperometric values were observed. At 50° C., the application of 1V for 15 seconds to the perfectly matched dsDNA:PNA triplex (SEQ ID NO:1+Probe No. 1) produced an average current of −0.25 μAmp as compared to values of −0.15 μAmp (a 40% reduction) and −0.06 μAmp (a 76% reduction) for the 1 bp mismatched dsDNA:PNA triplex (SEQ ID NO:2+Probe No. 1) and the 2 bp mismatched dsDNA:PNA triplex (SEQ ID NO:3+Probe No. 1), respectively (FIG. 1C). At 65° C., similar observations were noted when 1 V of electricity was applied for 15 seconds. Perfectly matched nucleic acid hybrids produced an average current of −0.37 μAmp compared with −0.16 μAmp (a 57% reduction) and −0.01 μAmp (a 97% reduction) for 1 bp and 2 bp mismatched hybrids, respectively (FIG. 1C). The application of 5 volts at high temperatures produced analogous results. While experiments performed at 50° C. generated average currents of −0.27 mAmp, −0.13 mAmp (a 52% reduction), and −0.08 mAmp (a 70% reduction), for perfectly matched hybrids, 1 bp mismatched hybrids, and 2 bp mismatched hybrids, respectively, experiments performed at 65° C. resulted in average current values of −0.31 mAmp, −0.14 mAmp (a 55% reduction), and −0.10 mAmp (a 68% reduction) for the same three respective groups (FIG. 1D). For all of the foregoing experiments, dsDNA was not denatured prior to triplex hybridization with the antiparallel PNA Probe No. 1.

Similar experiments were done at varying temperatures after the hybridization mixes had been heated to 65° C. and immediately allowed to cool. After cooling to room temperature (23° C.), applying 1V for 15 seconds to the perfectly matched sample (SEQ ID NO:1+Probe No. 1) produced an average current of −0.18 μAmp. By comparison, values of −0.06 μAmp (a 67% reduction) and −0.05 μAmp (a 72% reduction) for the 1 bp mismatched dsDNA:PNA triplex hybrid (SEQ ID NO:2+Probe No. 1) and the 2 bp mismatched dsDNA:PNA triplex hybrid (SEQ ID NO:3+Probe No. 1), were respectively observed (data not shown). When the samples were cooled from 65° C. to 50° C., similar observations were noted when 1 V was subsequently applied for 15 seconds. The perfectly matched sample (SEQ ID NO: 1+Probe No. 1) produced an average current of −0.23 μAmp compared with −0.11 μAmp (a 52% reduction) and −0.01 μAmp (a 96% reduction) observed for the 1 bp and 2 bp mismatched samples, respectively (data not shown). When 5V was applied after cooling to 23° C. or 50° C., the average current generated in the perfectly matched triplex hybrid (SEQ ID NO:1+Probe No. 1), the 1 bp mismatched triplex hybrid (SEQ ID NO:2+Probe No. 1), and the 2 bp mismatched triplex hybrid (SEQ ID NO:3+Probe No. 1) were: −0.15 mAmp, −0.09 mAmp (a 40% reduction), and −0.07 mAmp (a 53% reduction), respectively at 23° C., and −0.23 mAmp, −0.09 mAmp (a 61% reduction), and −0.09 mAmp (a 61% reduction), respectively at 50° C. (data not shown).

Pretreatment of hybridization mixes at 65° C. (the $T_m$ of the 50-mer dsDNA sequences) followed by cooling did not significantly affect the difference in conductance observed between perfectly complementary dsDNA:PNA triplexes and those containing 1 or 2 bp mismatches when measured directly at 23° C. or 50° C. (without preheating at 65° C.) when an antiparallel PNA probe was used. Clearly, the antiparallel PNA probe in the presence of the DNA intercalator YOYO-1 was able to form triplex structures with the dsDNA targets. Application of low levels of electricity (such as 1V or 5V) allowed the perfectly matched dsDNA:PNA triplex sequences to be distinguished from those containing 1 bp or 2 bp mutations, without prior denaturation of sequences.

Example 2

FIG. 2 demonstrates that the amperometric assay of the invention can also discriminate between perfectly matched dsDNA:PNA triplex hybrids and those containing 1 bp or 2 bp mismatches when the PNA probe used is in a parallel orientation with respect to the target DNA sequence. Probe No. 2 was a 15-mer PNA probe identical in sequence to Probe No. 1, but was synthesized to match the parallel orientation of the target DNA, instead of the conventional anti-parallel orientation. Probe No. 2 had the following structure (SEQ ID NO:9):

5'-H-TAT AGT AGA AAC CAC-Lys-CONH$_2$-3'

Experiments with assay conditions identical to those described in Example 1 were carried out with the sole difference that Probe No. 2 was used in place of Probe No. 1. When 1 volt was applied, the average current for a 1 bp mismatched dsDNA:PNA triplex (SEQ ID NO: 2+Probe No. 2), and a consecutive 2 bp mismatched dsDNA:PNA triplex (SEQ ID NO: 3+Probe No. 2), were respectively 25% and 32% lower at 23° C., respectively 30% and 23% lower at 50° C., and respectively 28% and 53% lower at 65° C. than that observed with the perfectly matched dsDNA:PNA triplex (SEQ ID NO:1+Probe No. 2) at matching temperatures (FIG. 2A).

Similar results were obtained when 5 V (instead of 1V) was applied for 15 seconds. Perfectly matched dsDNA:PNA hybrids at 23° C., 50° C. and 65° C. generated average currents of −0.15 mAmp, −0.24 mAmp and −0.17 mAmp, respectively (FIG. 2B). Incompletely complementary triplexes with a 1 bp mismatch and a 2 bp mismatch produced average currents that were 27% less (−0.11 mAmp) and 53% less (−0.07 mAmp), respectively at 23° C., 21% less (−0.19 mAmp) and 46% less (−0.13 mAmp), respectively at 50° C., and unchanged (−0.17mAmp) and 18% less (−0.14 mAmp), respectively at 65° C., than that achieved by the perfectly matched hybrid samples (FIG. 2B).

The results illustrated in FIGS. 2A and 2B indicated that when the parallel PNA Probe No. 2 was used, the differences in conductivity obtained between perfectly matched dsDNA:PNA triplexes and those containing 1 bp or 2 bp mismatches were less dramatic than that achieved with the antiparallel PNA Probe No. 1 (FIG. 1).

However, experiments involving parallel Probe No. 2 and the application of 5 V after the samples have been heated to 65° C. and immediately allowed to cool disclosed amperometric measurements which demonstrated enhanced signaling differences between perfectly matched dsDNA:PNA triplexes and the 1 bp or 2 bp mismatched dsDNA:PNA triplexes (FIG. 2C). The perfectly matched hybrids (SEQ ID NO:1+Probe No. 2), the 1 bp mismatched hybrids (SEQ ID NO:2+Probe No. 2) and the 2 bp mismatched hybrids (SEQ ID NO:3+Probe No. 2) yielded average conductance values of −0.19 mAmps, −0.08 mAmps and −0.06 mAmps, respectively at 23° C., −0.17 mAmps, −0.09 mAmps and −0.07 mAmps, respectively at 50° C., and −0.23 mAmps, −0.13 mAmps and −0.08 mAmps, respectively at 65° C. This translated to reductions in conductivity of 58% and 35 68% at 23° C., 47% and 59% at 50° C., and 43% and 65% at 65° C. for the 1 bp and 2 bp mismatched samples, respectively, when compared to the values achieved by the perfectly complementary samples (FIG. 2C).

Therefore, both antiparallel and parallel PNA probes in the amperometric assay are capable of discriminating between perfectly complementary dsDNA targets and incompletely complementary dsDNA targets containing 1 bp or 2 bp mutations.

Example 3

Probe No. 3 was a 15-mer ssDNA probe identical in sequence and orientation to the 15-mer antiparallel PNA Probe No. 1 (SEQ ID NO:8). Probe No. 3 had the following structure:

5'-CAC CAA AGA TGA TAT-3'

The specificity of the amperometric assay was further investigated by reacting ssDNA Probe No. 3 with the 50-mer wild-type and mutant dsDNA target sequences in the absence of prior denaturation. The assay conditions were identical to that described in Example 1.

Enhanced by the DNA intercalator YOYO-1, dsDNA:ssDNA triplexes were formed between 30° C. and 65° C. Upon 1 volt treatment, the perfectly matched DNA triplex, consisting of SEQ ID NO:1+Probe No. 3, yielded the highest conductivity values (FIG. 3A). In contrast, incompletely complementary probe and target combinations generating a 1 bp mismatch (SEQ ID NO:2+Probe No. 3), and a consecutive 2 bp mismatch (SEQ ID NO:3+Probe No. 3), resulted in average conductance values that were 14% and 64% lower at 23° C., 30% and 70% lower at 50° C., and 25% and 72% lower at 65° C., respectively, than that observed with the perfectly complementary sequences at matching temperatures (FIG. 3A). The application of a higher voltage (5V) to these samples resulted in greater amperometric differences observed between perfectly matched and mismatched samples, than that obtained at 1 V, particularly at lower temperatures. After a 5V treatment for 15 seconds, the average currents for the 1 bp mismatched DNA triplex and the 2 bp mismatched DNA triplex were 54% and 78% lower, respectively at 23° C., 68% and 70% lower, respectively at 50° C., and 33% and 61% lower, respectively at 65° C., than that observed with the perfectly matched DNA triplex at matching temperatures (FIG. 3B).

In similar electricity experiments, the hybridization mixes were heated to 65° C. and were either maintained at this temperature or immediately allowed to cool to 50° C. or 23° C. prior to application of 1V or 5V. A 1V treatment for 15 seconds to the perfectly matched DNA triplex sequences (SEQ ID NO:1+Probe No. 3) produced the highest conductance values at 23° C., 50° C. and 65° C. (FIG. 3A). The DNA triplexes containing a 1 bp mismatch (SEQ ID NO:2+Probe No. 3) or a 2 bp mismatch (SEQ ID NO:3+Probe No. 3) were less conductive by 21% and 63%, respectively at 23° C., by 18% and 74%, respectively at 50° C., and by 12% and 106%, respectively at 65° C. (FIG. 3A). Similarly, when 5V were applied for 15 seconds to pre-heated samples, the average conductance values for the 1 bp mismatched DNA triplexes and the 2 bp mismatched DNA triplexes were reduced by 24% and 104%, respectively at 23° C., by 42% and 44%, respectively at 50° C., and by 38% and 102%, respectively at 65° C., when compared to the average conductance values generated by the perfectly matched DNA triplexes (FIG. 3B).

The observation that the antiparallel PNA probe (FIG. 1) and ssDNA probe (FIG. 3) behaved in a similar fashion in the amperometric assay, suggested that the backbone of the nucleic acid entity used as the probe was not particularly important. The presence of YOYO-1 allowed the dsDNA targets and the ssDNA probe to form a triple helix conformation capable of generating different electrical charges depending on the level of sequence complementarity between the target and the probe in solution. As the degree of mismatch between the probe and the target increased, the level of conductance decreased, proving the reliability of the amperometric assay when a natural DNA probe was used in the absence of prior denaturation.

Example 4

In the amperometric assays illustrated in Examples 1 to 3, the DNA intercalator YOYO-1 was added to the solution containing the hybridization mixes. Intercalation by YOYO-1 facilitated the formation of the dsDNA:PNA triplexes and dsDNA:ssDNA triplexes. The possibility of utilizing an intercalator moiety covalently tethered to a ssDNA probe in the amperometric assay was evaluated in Example 4.

Acridine is an alternative dsDNA intercalator, that also possesses the ability to intercalate into triplex nucleic acid structures, thereby stabilizing the triple helix formation.

See, e.g., Kukreti et al., "Extension of the range of DNA sequences available for triple helix formation: stabilization of mismatched triplexes by acridine-containing oligonucleotides." 25 Nucleic Acids Research 4264-4270 (1997). A ssDNA probe containing an acridine molecule (Glen Research, Sterling, Va., USA) covalently attached at the 3' end was synthesized on a DNA synthesizer (Expedite 8909, PerSeptive Biosystems) and purified by HPLC.

Probe No. 4 was a 15-mer ssDNA probe identical in sequence and orientation to the 15-mer Probe No. 3 (and thus also identical in sequence and orientation to the 15-mer antiparallel PNA Probe No. 1 (SEQ ID NO:8)) but with the addition of an acridine moiety at the 3' position. The probe had the following structure:

5'-CAC CAA AGA TGA TAT-acridine-3'

The hybridization reaction mixture (80 µl) contained the following: 2 pmoles of target dsDNA, 2 pmoles of ssDNA Probe No. 4 and 0.5×TBE. Samples were placed into a 3 mm quartz cuvette and were subjected to 5V DC electrification for 11 seconds at 23° C. The current and temperature were monitored as described in Example 1.

As shown in FIG. 4, the ssDNA Probe No. 4 was able to hybridize with the 50-mer perfectly matched dsDNA target (SEQ ID NO:1) as a result of the stable intercalation of the covalently tethered acridine moiety, generating an average current of −0.53 mAmp. By comparison, the less stable DNA triplexes containing a 1 bp mismatch (SEQ ID NO:2+Probe No. 4) or a 2 bp mismatch (SEQ ID NO:3+Probe No. 4) produced average currents that were 52% and 66% lower, respectively, than that achieved by the perfectly matched DNA triplex, when normalized against the control (Probe No. 4 without target DNA) (FIG. 4).

Therefore, the acridine attached to a ssDNA probe was equally as efficient as untethered YOYO-1 in forming triple DNA helices that generated different electrical currents depending on the level of sequence complementarity between the target and the probe in the amperometric assay.

Example 5

Sense and antisense 15-mer ssDNA target sequences, derived from exon 10 of the human cystic fibrosis gene, were synthesized, purified and annealed as described in Example 1. DsDNA oligonucleotides were dissolved in ddH$_2$0 at a concentration of 1 pmole/µl.

SEQ ID NO:4 was a 15-mer dsDNA target sequence derived from SEQ ID NO:1, designed to be completely complementary to Probe No. 1.

Sequence for the sense strand of the wild-type target DNA (SEQ ID NO:4):

5'-ATA TCA TCT TTG GTG-3'.

Sequence for the antisense strand of the wild-type target DNA (SEQ ID NO:4):

5'-CAC CAA AGA TGA TAT-3'.

The predicted melting temperature (T$_m$) of dsDNA (SEQ ID NO:4) is 40° C.

SEQ ID NO:5 was a 15-mer mutant dsDNA target sequence identical to wild-type target DNA (SEQ ID NO:4) except for a one base pair mutation (underlined), at which the sequence TTT was changed to TAT.

Sequence for the sense strand of the mutant target DNA (SEQ ID NO:5):

5'-ATA TCA TCT ATG GTG-3'.

Sequence for the antisense strand of the mutant target DNA (SEQ ID NO:5):

5'-CAC CAT AGA TGA TAT-3'.

The predicted melting temperature (T$_m$) of dsDNA (SEQ ID NO:5) is 40.0° C.

SEQ ID NO:6 was a 15-mer mutant dsDNA target sequence identical to wild-type target DNA (SEQ ID NO:4) except for a consecutive two base pair mutation (underlined), at which the sequence ATC was changed to GGC.

Sequence for the sense strand of the mutant target DNA (SEQ ID NO:6):

5'-ATA TCG GCT TTG GTG-3'.

Sequence for the antisense strand of the mutant target DNA (SEQ ID NO:6):

5'-CAC CAA AGC CGA TAT-3'.

The predicted melting temperature (T$_m$) of dsDNA (SEQ ID NO:6) is 44.0° C.

SEQ ID NO:7 was a 15-mer mutant dsDNA target sequence identical to wild-type target DNA (SEQ ID NO:4) except for a separated three base pair mutation (underlined), wherein three 1 bp mutations were separated by 3 base pairs each. The sequences ATC, TCT and TGG were changed to ACC, TAT and TAG, respectively.

Sequence for the sense strand of the mutant target DNA (SEQ ID NO:7):

5'-ATA CCA TAT TTA GTG-3'.

Sequence for the antisense strand of the mutant target DNA (SEQ ID NO:7):

5'-CAC TAA ATA TGG TAT-3'.

The predicted melting temperature (T$_m$) of dsDNA (SEQ ID NO:7) is 38.0° C.

The hybridization reaction mixture (80 µl) contained the following: 2 pmoles of target dsDNA, 2 pmoles of parallel PNA Probe No. 2, 0.5×TBE and 250 nM of the DNA intercalator YOYO-1. The reaction mixtures were incubated at 95° C. for 5-10 minutes to allow denaturation, and then maintained at 65° C. until assayed. Samples were placed into a quartz cuvette, irradiated with an argon ion laser beam having a wavelength of 488 nm and monitored for fluorescent emission at 65° C. Concurrent temperature measurements were achieved by a software-controlled temperature probe placed directly into each sample. The maximum fluorescent intensity occurred at a wavelength of 536 nm, indicative of intercalation of YOYO-1 in the PNA:DNA hybrids. As a second assay, following the initial laser irradiation of each sample, the same samples were subjected to 1V DC electrification for 4 seconds. During the final second of electrification the samples were irradiated a second time with the argon ion laser and monitored for fluorescent emission at 65° C. Fluorescent intensities were plotted as a function of wavelength for each sample analyzed.

SsDNA:PNA hybrids consisting of perfectly complementary sequences (SEQ ID NO:4+Probe No. 2) allowed maximum intercalation of YOYO-1, yielding the highest fluorescent intensities (FIG. 5A). The fluorescent intensities for a 1 bp mismatched ssDNA:PNA hybrid (SEQ ID NO:5+Probe No. 2), a consecutive 2 bp mismatched ssDNA:PNA hybrid (SEQ ID NO:6+Probe No. 2), and a separated 3 bp mismatched ssDNA:PNA hybrid (SEQ ID NO:7+Probe No. 2) were all lower than that observed with the perfectly matched ssDNA:PNA hybrid at 65° C. (FIG. 5 and data not shown). As the degree of mismatch between the probe and the target increased, the level of intercalation by YOYO-1 diminished and hence the level of fluorescent intensity decreased. Only background levels of fluorescence were observed when no DNA or PNA was present (YOYO-1 alone) (FIG. 5A).

When the perfectly matched ssDNA:PNA hybrids were subjected to 1V of electricity for 4 seconds at 65° C., the fluorescent intensity remained relatively constant, decreasing by only 2% (FIG. 5A). In contrast, application of 1V to the incompletely complementary duplexes containing a 1 bp mismatch (FIG. 5B), a 2 bp mismatch (FIG. 5C) and a 3 bp mismatch (data not shown) produced fluorescent intensities that were 18%, 39% and 71% lower, respectively, than that achieved with the same samples irradiated in the absence of electricity. Treatment with low levels of electricity (such as 1V) further diminished the stability of the ssDNA:PNA hybrids containing bp mismatches. As the degree of sequence complementarity between the probe and the target decreased, the level of fluorescent intensity diminished dramatically in the presence of electricity, providing a highly reliable and accurate second assay to differentiate between perfectly matched sequences and those containing 1 bp, 2 bp or 3 bp mutations.

Example 6

The hybridization assay in Example 5 was performed after denaturation of the dsDNA target sequences and measured ssDNA:PNA hybrid formation at a temperature above the melting point (T$_m$) of the dsDNA targets. Example 6 will demonstrate the reliability of the fluorescent intensity assay in the absence and presence of applied electricity to differentiate between perfect matches and base pair mismatches without the requirement for prior denaturation.

The hybridization reaction mixture (80 µl) contained the following: 4 pmoles of target dsDNA, 4 pmoles of antiparallel PNA Probe No. 1, 0.5×TBE and 250 nM of the DNA intercalator YOYO-1. Samples were placed into a quartz cuvette, irradiated with an argon ion laser beam having a wavelength of 488 nm for 80 msec and monitored for fluorescent emission at 23° C. Concurrent temperature measurements were achieved by a software-controlled temperature probe placed directly into each sample. The maximum fluorescent intensity occurred at a wavelength of 536 nm, indicative of intercalation of YOYO-1 in the PNA:DNA hybrids. As a second assay, following the initial laser irradiation of each sample, the same samples were subjected to 20V DC electrification for 4 seconds. Immediately after 3 seconds of electrification the samples were irradiated a second time with the argon ion laser for 80 msec and monitored for fluorescent emission at 23° C. Fluorescent intensities were plotted as a function of wavelength for each sample analyzed.

Enhanced by the intercalator YOYO-1, dsDNA:PNA triplexes were formed at 23° C. The highest fluorescent intensity was achieved when the wild-type 50-mer dsDNA target sequence (SEQ ID NO:1) was hybridized with the 15-mer antiparallel PNA Probe No. 1 (FIG. 6). By comparison, the fluorescent intensities for a 1 bp mismatched dsDNA:PNA triplex (SEQ ID NO:2+Probe No. 1) and a consecutive 2 bp mismatched dsDNA:PNA triplex (SEQ ID NO:3+Probe No. 1) were 60% and 91% lower, respectively, than that observed with the perfectly matched dsDNA:PNA triplex at 23° C. (FIG. 6). When no DNA or PNA was present in the reaction mixture containing YOYO-1, only background levels of fluorescence were observed.

The difference in fluorescent intensities obtained by the perfectly complementary triplexes and those containing 1 bp or 2 bp mismatches were significantly greater than that achieved between perfectly matched duplexes and incompletely complementary duplexes (compare FIGS. 5 and 6). Clearly the fluorescent intensity assay of triplex formation possessed enhanced discriminatory ability to detect base pair mismatches.

Moreover, even further discrimination between wild-type and mutated sequences was possible with the secondary application of electricity. A 20V treatment for 3 seconds to the perfectly matched dsDNA:PNA triplexes produced a fluorescent intensity spectrum virtually identical to that achieved by the same sample not subjected to electricity (FIG. 6). However, application of 20V for 3 seconds to the incompletely complementary triplexes containing a 1 bp mismatch and a 2 bp mismatch produced fluorescent intensities that were 23% and 71% lower, respectively, than that obtained with the same samples irradiated in the absence of electricity (FIG. 6). The 20V treatment of electricity did not affect the stability of the perfectly complementary triplexes, but weakened the stability of the dsDNA:PNA triplexes containing base pair mismatches at a level dependent on the degree of sequence complementarity between the probe and the target. Therefore, the application of electricity to the fluorescent intensity assay provided an even more highly reliable assay to distinguish between wild-type sequences and those containing 1 bp or 2 bp mutations, without prior denaturation of sequences.

While the invention has been described in detail and with reference to specific examples thereof, it will be apparent to one skilled in the art that various changes and modifications can be made without departing from the spirit and scope thereof.

What is claimed is:

1. A method for assaying sequence-specific hybridization, said method comprising:
providing a target comprising at least one target biopolymer sequence;
providing a probe comprising at least one probe biopolymer sequence;
adding said probe and said target to a binding medium to provide a test sample;
applying a first stimulus to said test sample to provide a first stimulated test sample;
detecting a first signal from said first stimulated test sample, wherein said first signal is correlated with a binding affinity between said probe and said target;
applying a second stimulus to said first stimulated test sample to provide a second stimulated test sample;
detecting a second signal from said second stimulated test sample, wherein said second signal is correlated with said binding affinity between said probe and said target; and
comparing said first signal and said second signal to accomplish said assaying;
wherein: (a) at least one label is provided in said test sample, (b) said first stimulus, said second stimulus, said first signal and said second signal are photonic or electronic, (c) at least one of said first stimulus and said second stimulus is photonic, (d) when said first stimulus and said second stimulus are photonic, an intermediate electronic stimulus is applied to said test sample after said first stimulus and before said second stimulus, (e) said probe biopolymer sequence and said target biopolymer sequence contain nucleobases and said probe hybridizes specifically with said target to form a homologous duplex, a homologous triplex, a homologous quadruplex, a Watson-Crick triplex or a Watson-Crick quadruplex, and (f) said method is conducted without separating probe-target complexes from free probes and targets.

2. The method of claim 1, wherein said first stimulus is photonic and said second stimulus is electronic.

3. The method of claim 1, wherein said first stimulus is photonic and said second stimulus is photonic.

4. The method of claim 1, wherein said first stimulus is electronic and said second stimulus is photonic.

5. The method of claim 1, wherein application of said second stimulus is at least partially coextensive with application of said first stimulus.

6. The method of claim 1, wherein said first signal is photonic and said second signal is electronic.

7. The method of claim 1, wherein said first signal is photonic and said second signal is photonic.

8. The method of claim 1, wherein said first signal is electronic and said second signal is photonic.

9. The method of claim 1, wherein at least one of said first stimulus and said second stimulus is a laser beam.

10. The method of claim 1, wherein said first stimulus, said second stimulus or said intermediate electronic stimulus is electric voltage.

11. The method of claim 1, wherein said at least one label transfers energy to at least one other label to generate at least one of said first signal and said second signal.

12. The method of claim 1, wherein said at least one label is chemiluminescent or electrochemiluminescent.

13. The method of claim 1, wherein said at least one label is an electron spin label.

14. The method of claim 1, wherein said probe hybridizes specifically with said target to form a homologous duplex substantially free of Hoogsteen bonding.

15. The method of claim 1, wherein said probe hybridizes specifically with said target to form a homologous or Watson-Crick triplex substantially free of Hoogsteen bonding.

16. The method of claim 1, wherein said probe hybridizes specifically with said target to form a homologous or Watson-Crick quadruplex substantially free of Hoogsteen bonding and free of G-G quartets.

17. The method of claim 1, wherein said probe is a nucleic acid analog containing at least one of an uncharged backbone, a partially charged backbone, a cationic moiety, a crosslinking agent, a crosslinking sidechain and a nucleobase analog.

18. The method of claim 1, wherein at least one of said probe biopolymer sequence and said target biopolymer sequence contains an amino acid sequence.

19. The method of claim 1, further comprising:
applying at least one additional stimulus to said second stimulated test sample to provide an additionally stimulated test sample;
detecting at least one additional signal from said additionally stimulated test sample, wherein said at least one additional signal is correlated with said binding affinity between said probe and said target; and
comparing said first signal, said second signal and said at least one additional signal to accomplish said assaying.

20. The method of claim 19, wherein said first stimulus, said second stimulus and said at least one additional stimulus are different from each other.

21. The method of claim 19, wherein at least one of said first stimulus, said second stimulus and said at least one additional stimulus is applied non-continuously.

22. The method of claim 1, wherein at least one of said first stimulus and said second stimulus is applied non-continuously.

23. The method of claim 1, wherein at least one of said probe and said target is bonded to a substrate, surface, partition, membrane or electrode.

24. The method of claim 1, wherein said at least one label is not covalently bound to said probe or said target.

25. The method of claim 1, wherein said at least one label is an intercalating agent.

26. The method of claim 25, wherein said at least one label is not covalently bound to said probe or said target.

27. The method of claim 26, wherein said first stimulus is directly applied to said test sample and said second stimulus is directly applied to said first stimulated test sample.

28. The method of claim 1, wherein said first stimulus, said second stimulus or said intermediate electronic stimulus is electric voltage applied to said test sample for 15 seconds or less.

29. The method of claim 1, wherein said first stimulus, said second stimulus or said intermediate electronic stimulus is electric voltage effective to destabilize imperfectly matched hybridization partners and ineffective to destabilize perfectly matched hybridization partners.

30. A method for assaying sequence-specific hybridization, said method comprising:
providing a target;
providing a probe, wherein at least one of said probe and said target comprises at least one biopolymer sequence;
adding said probe and said target to a binding medium to provide a test sample;
applying a first stimulus directly to said test sample to provide a first stimulated test sample;

detecting a first signal from said first stimulated test sample, wherein said first signal is correlated with a binding affinity between said probe and said target;

applying a second stimulus directly to said first stimulated test sample to provide a second stimulated test sample;

detecting a second signal from said second stimulated test sample, wherein said second signal is correlated with said binding affinity between said probe and said target; and comparing said first signal and said second signal to accomplish said assaying;

wherein: (a) at least one label is an intercalating agent provided in said test sample and is not covalently bound to said probe or to said target, (b) said first stimulus, said second stimulus, said first signal and said second signal are photonic or electronic, (c) at least one of said first stimulus and said second stimulus is photonic, (d) when said first stimulus and said second stimulus are photonic, an intermediate electronic stimulus is applied to said test sample after said first stimulus and before said second stimulus and (e) said method is conducted without separating probe-target complexes from free probes and targets.

31. The method of claim 30, wherein at least one of said probe and said target is a protein, a peptide or a lipid membrane.

32. The method of claim 30, wherein one of said probe or said target is not a biopolymer.

33. The method of claim 30, wherein said first stimulus, said second stimulus or said intermediate electronic stimulus is electric voltage applied to said test sample for 15 seconds or less.

34. The method of claim 30, wherein said first stimulus, said second stimulus or said intermediate electronic stimulus is electric voltage effective to destabilize imperfectly matched hybridization partners and ineffective to destabilize perfectly matched hybridization partners.

* * * * *